(12) United States Patent
Khan et al.

(10) Patent No.: US 6,200,730 B1
(45) Date of Patent: Mar. 13, 2001

(54) SPIN-TRANSITION PARENT COMPOUNDS

(75) Inventors: Olivier Khan, Massy; Charlotte Jay, Paris; Jonas Krober, Paris; Renee Claude, Paris; Francoise Groliere, Nogent-sur-Marne, all of (FR)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/464,857

(22) Filed: Dec. 16, 1999

Related U.S. Application Data

(60) Division of application No. 08/383,170, filed on Feb. 3, 1995, now Pat. No. 6,043,008, which is a continuation-in-part of application No. 08/247,383, filed on May 23, 1994, now Pat. No. 5,582,900, which is a continuation-in-part of application No. 07/979,104, filed on Nov. 20, 1992, now abandoned.

(30) Foreign Application Priority Data

Feb. 3, 1994 (FR) .................................................. 94 01224

(51) Int. Cl.$^7$ ............................... G03C 1/64; G11B 7/24
(52) U.S. Cl. .................................... 430/270.1; 430/495.1; 430/964; 252/584; 252/586
(58) Field of Search ............................. 430/270.1, 495.1, 430/964; 252/584, 586

(56) References Cited

U.S. PATENT DOCUMENTS 5,582,900 * 12/1996 Khan et al. ........................... 428/195

FOREIGN PATENT DOCUMENTS 0 543 465 * 5/1993 (EP) .

* cited by examiner

Primary Examiner—John A. McPherson
(74) Attorney, Agent, or Firm—Ernestine C. Bartlett

(57) ABSTRACT

A chemical composition is provided for the manufacture of devices for storing and/or displaying information, comprising a network having a molecule which is formed from a metallic element $Fe_{(II)}$ which is bonded to a 1-2-4 triazole ligand (H-Trz), which molecule further comprises one or more than one anions A selected from $BF_4^-$, $ClO_4^-$, $CO_3^{2-}$, $Br^-$, $Cl^-$, in accordance with the formulation:

$$Fe_{II} (H\text{-}Trz)_3 A_2,$$

characterized in that this composition is used in the pure state in either one of the two crystalline phases ($\alpha$, $\beta$) at least one of which, referred to as the second phase ($\beta$), can be thermally induced on the basis of the other phase, referred to as the first phase ($\alpha$), at a temperature which is equal to or higher than a first reference temperature (To), which phases each show thermally inducible spin transitions between a low-spin state at a low first temperature ($T_{\alpha 1}$, $T_{\beta 1}$) and a high-spin state at a high second temperature ($T_{\alpha 2}$, $T_{\beta 2}$), the spin transitions which are associated with each phase being accompanied by a similar abrupt change in color of the compound and taking place in accordance with hysteresis cycles at different temperatures of the two phases, wherein the hysteresis cycle ($T_{\alpha 1}$, $T_{\alpha 2}$) associated with the first phase ($\alpha$) occurs at a temperature which is higher than a second reference temperature ($T_R$), and the hysteresis cycle ($T_{\beta 1}$, $T_{\beta 2}$) associated with the second phase ($\beta$) occurs at a temperature below the second reference temperature ($T_R$), the first reference temperature (To) being higher than the second reference temperature ($T_R$) and the highest spin-transition temperature ($T_{\alpha 2}$).

8 Claims, 2 Drawing Sheets

SPIN-TRANSITION PARENT COMPOUNDS

CROSS REFERENCE TO RELATED APPLICATIONS

This application is a divisional of application Ser. No. 08/383,170, filed Feb. 3, 1995, now U.S. Pat. No. 6,043,008, which is a continuation-in-part of application Ser. No. 08/247,383 filed May 23, 1994, now U.S. Pat. No. 5,582,900, which is a continuation-in-part of application Ser. No. 07/979,104, filed Nov. 20, 1992, now abandoned.

Spin-transition parent compounds and devices having means for writing, storing and erasing, which comprise an active medium containing at least one of said compounds.

The invention relates to spin-transition parent compounds and to methods of manufacturing said compounds.

The invention also relates to devices having means for writing, storing and erasing, which comprise an active medium containing at least one of said parent compounds. The invention further relates to methods of utilizing these devices.

The invention is used in the field of information storage and processing devices and/or data display devices.

In Patent Application EP-0 543 465, there is already disclosed a family of compounds which can suitably be used to form materials which can be written and erased by means of heat and whose operating range corresponds to the ambient temperature range.

This family is formed from a network of molecules, comprising:

A) a metal, such as iron $Fe_{II}$ or $Fe_{III}$, or cobalt $Co_{II}$,

B) ligands which are bonded to this metal, such as:
   a substituted 1-2-4 triazole of the abridged formula R-Trz, wherein R is an alkyl $C_n H_{2n+1}$

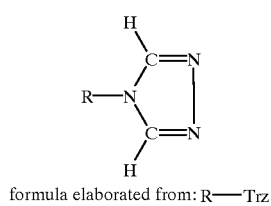

formula elaborated from: R—Trz a 1-2-4 triazolate of the abridged formula Trz⁻

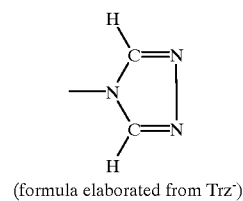

(formula elaborated from Trz⁻)

C) an anion which is selected from the group formed by $BF_4^-$, $ClO_4^-$, $CO_3^{2-}$, $Br^-$, $Cl^-$ D) and at least one water molecule $H_2O$ which is not covalently bonded to the metal complex, but whose presence in the network can be attributed to an hygroscopic agent selected from the precursors of the metal nucleus, E) and a doping agent, which is an aminotriazole of the abridged formula R'-Trz, wherein R' is an amine $N-C_n H_{2n+1}$

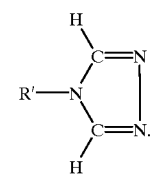

(formula elaborated from R'—Trz)

The general formula of the molecules of the family described in the above-mentioned document can be expressed as follows:

$$M_{II}[(R\text{-}Trz)_2(Trz^-)]_{1-x} (R'\text{-}Trz)_x A, n\, H_2O.$$

In this formula, M is the metal and A is the anion,

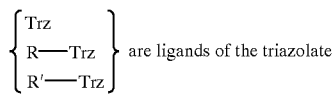 are ligands of the triazolate and substituted triazole types, the respective proportions of which are governed by the value x of the concentration, and n is the number of water molecules $H_2O$ which are bonded in a non-covalent manner to the molecule of the metal complex.

In addition, in this formula the concentration value x is small, so that the proportion of the ligand R'-Trz is small and, in fact, constitutes a doping agent which acts on the intrinsical properties of the material.

The above-mentioned, exemplary molecules which are selected from said general family include:

$$Fe_{II}[(HTrz)_2(Trz^-)]_{0.9} (NH_2\text{-}Trz)_{0.1} (BF_4^-), 6H_2O$$

wherein

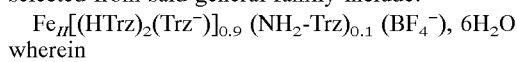
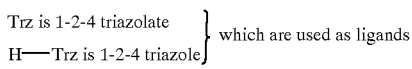

which are used as ligands $NH_2$-Trz is aminotriazole which is used as a dopant.

A method of preparing compounds of this general family consists in combining a salt of the metal (for example $Fe(ClO_4^-)_2$) with the ligands in an acid solution, thereby forming a precipitate. Subsequently, the precipitate is separated from the solution. Said precipitate is obtained in powdered form. By using an excess of the metal salt, a certain quantity of water is captured.

The compounds of the general family described in EP 0 543 465 exhibit spin transitions, between a low-spin state (LS) and a high-spin state (HS), which are induced only by heat, and which involve electronic and structural changes of the molecules. Said changes bring about an abrupt change of the absorption spectrum of the molecules and hence of the colour of the compounds, and the electronic energy levels also being different.

In the low-spin state (LS), the compounds are dark purple, whereas in the high-spin state (HS), these compounds are chalk-white. In addition, each of the high-spin (HS) and low-spin (LS) states is perfectly stable if the compounds are subjected to an average temperature, referred to as average critical temperature, which ranges between the maximum and minimum temperatures in the high-spin state or low-spin state.

Studies of these materials have revealed that, apart from spin transition, they exhibit a delay effect which can be attributed to intermolecular cooperativity, resulting in a hysteresis phenomenon which, dependent upon the material used, may range from several degrees centigrade to several tens of degrees centigrade, between −20 and 100° C., i.e. in a temperature range which is appropriate for industrial applications.

When a thermal perturbation is applied, the cooperative effect brings about that either:

all molecules simultaneously undergo a transition within an aggregate, or none of the molecules undergoes said transition.

The compounds of the general family disclosed in EP 0 543 465 can also be used as memory materials which can be thermally written and erased and optically read and, thus, can also be used to store information, process information or display information.

The document in accordance with the state of the art EP 0 543 465, discloses that the temperature range in which the compounds operate depends to a substantial extent on the properties of the ligand selected as the dopant.

The spin transition of the known compounds presupposes the existence of two potential wells, one of which corresponds to the low-spin state (LS) and the other corresponds to the high-spin state (HS). These potential wells are separated by a potential barrier. The bottom of each of the potential wells corresponds, respectively, to a first and a second energy level, the energy level of the bottom of the high-spin well being higher than the energy level of the bottom of the low-spin well.

The application of a thermal perturbation to one of the compounds of said family, which has first been brought to a stable low-spin state (LS) in which the electrons are trapped in the first potential well, results in the induction of unstable, excited high-spin states, after which the electrons relax via allowed transitions, while following a principal relaxation path, being the path of the second potential well, which corresponds to a perfectly stable high-spin state in a specific temperature range. The electrons remain trapped in the second potential well corresponding to the high-spin state (HS) and do not spontaneously return to the first potential well corresponding to the low-spin state (LS) due to the hysteresis phenomenon. To return to the low-spin state (LS), the compound must be cooled to a temperature which lies well within the hysteresis range.

Meanwhile, the compounds of the family known from the above-mentioned document exhibit too small a hysteresis amplitude in the ambient temperature range in which they are to be used as materials for recording or storing information. For example, exemplary compound No.5 of EP 0 543 465

$Fe_{II}[(HTrz)_2(Trz^-)]_{0.9} (NH_2-Trz)_{0.1} (BF_4^-), 6H_2O$ has a critical temperature in the range from 20 to 25° C. and a hysteresis amplitude of only 10 to 20°.

It is an object of the invention to provide compounds which are selected from compounds which:

present thermally induced spin transitions and hence can be thermally written and erased, can be optically read, exhibit stable spin states, have a critical temperature in the ambient temperature range, exhibit a hysteresis effect which has a much larger amplitude than that of the compounds of the above-mentioned document EP 0 543 465, so that a better control of both the writing and erasing operations is possible and, in particular, the temperatures at which writing or erasing take place meet the standards imposed by the manufacturers of display devices, said standards being:

$T \leq 5°$ C. for erasing $T > 50°$ C. for writing.

These objects are achieved by means of a spin-transition parent compound in powder form, comprising a network having a molecule which is formed from a complex in which iron ($Fe_{II}$) is bonded to a 1-2-4 triazole ligand (H-Trz), said molecule further comprising an anion $(A)_2$ which is selected from $BF_4^-$, $ClO_4^-$, $Br^-$, $CO_3^{2-}$, and, dependent upon the anion, said molecule corresponding to the formula:

a) $Fe_{II}(H-Trz)_3 (BF_4^-)_2$ b) $Fe_{II}(H-Trz)_3 (ClO_4^-)_2$ c) $Fe_{II}(H-Trz)_3 (Br^-)_2$ d) $Fe_{II}(H-Trz)_3 (Cl^-)_2$ e) $Fe_{II}(H-Trz)_3 (CO_3^{2-})$

In an alternative embodiment in accordance with the the invention, there is proposed a spin-transition parent compound in powder form, comprising a network having a molecule which is formed from a complex in which iron ($Fe_{II}$) is bonded to a 1-2-4 triazole ligand (H-Trz), said molecule further comprising an anion $(A)_2$ which is selected from $BF_4^-$, $ClO_4^-$, $Br^-$, $ClO_3^{2-}$, and, dependent upon the anion, said molecule corresponding to the formula:

a) $Fe_{II}(H-Trz)_3 (BF_4^-)_2, H_2O$ b) $Fe_{II}(H-Trz)_3 (ClO_4^-)_2, H_2O$ c) $Fe_{II}(H-Trz)_3 (Br^-)_2, H_2O$ d) $Fe_{II}(H-Trz)_3 (Cl^-)_2, H_2O$ e) $Fe_{II}(H-Trz)_3 (CO_3^{2-}), H_2O$ wherein one water molecule per molecule of the iron complex is present in the network, said water molecule only being bonded to the 1-2-4 triazole ligand (H-Trz) by a hydrogen bond.

This parent compound has a surprising effect, which is not known to be produced by the general family described in European Patent Application EP 0 543 465. Said surprising effect consists in that the parent compound in accordance with the invention has two crystalline phases $(\alpha, \beta)$ at least one of which, referred to as the second phase $(\beta)$, can be thermally induced on the basis of the other phase, referred to as the first phase $(\alpha)$, at a temperature which is equal to or higher than a first reference temperature (To). Said surprising effect is not described in EP 0 543 465 and, in accordance with the invention, the compounds of the general family, excluding those selected herein to form the present parent compound, do not produce this effect.

These two crystalline phases $(\alpha, \beta)$ each exhibit thermally inducible spin transitions between a low-spin state at a low first temperature $(T_{\alpha 2}, T_{\beta 2})$ and a high-spin state at a high second temperature $(T_{\alpha 1}, T_{\beta 1})$, said spin transitions which are associated with each phase being accompanied by an abrupt change in colour of the compound between a first colour and a second colour, which changes in colour are the same for both phases. Said spin transition of each phase takes place in accordance with hysteresis cycles at temperatures which are different for each of the two phases. The hysteresis cycle $(T_{\alpha 1}, T_{\alpha 2})$ associated with the first phase $(\alpha)$ occurs at a temperature which is higher than a second reference temperature $(T_R)$, and the hysteresis cycle $(T_{\beta 1}, T_{\beta 2})$ associated with the second phase $(\beta)$ occurs at a temperature below the second reference temperature $(T_R)$, the first reference temperature (To) being higher than the second reference temperature $(T_R)$ and the highest spin-transition temperature $(T_{\alpha 1})$.

These novel and unexpected properties enable this parent compound to be used more satisfactorily in the preparation of active media for information display devices, information storage devices and information processing devices.

The invention will be explained in greater detail with reference to the accompanying schematic drawings, in which FIG. 1 shows the enthalpy H which corresponds to the spin transition of a quantity of a compound, for example 1 mole, as a function of arbitrary molecular coordinates, for example the metal-ligand distance D;

Figure 1:
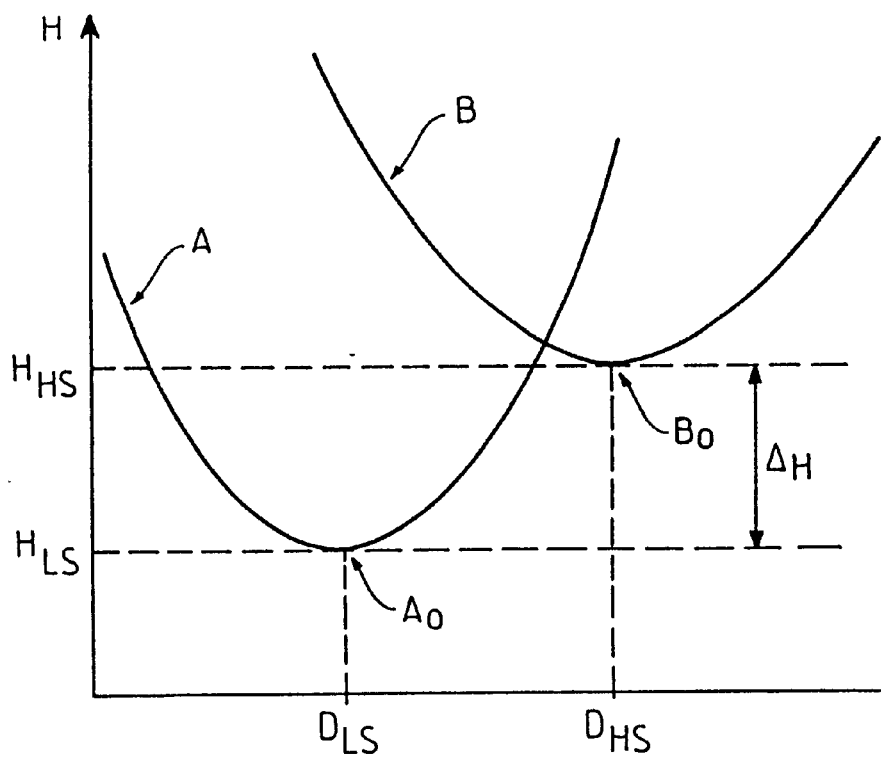

I CHEMICAL FORMULATION OF THE PARENT COMPOUNDS SELECTED IN ACCORDANCE WITH THE INVENTION

In accordance with the invention, a description is given of a sub-family of compounds selected from the general family of compounds disclosed in Patent Application EP 0 543 465. The terms "spin-transition compounds" and "spin-transition parent compounds" are used interchangeably to denote the products selected in accordance with the invention from said general family.

As stated hereinabove, the compounds of the known general family exhibit spin-transition properties and a hysteresis phenomenon between the low-spin state (LS) and the high-spin state (HS). The critical temperature of the known compounds lies in the ambient temperature range, at approximately 20° C., but they have a small hysteresis amplitude, typically, of approximately 10 degrees.

The hysteresis amplitude of the compounds between their low-spin state (LS) and high-spin state (HS) is expanded by means of the following selection of compounds.

It has been found that the compounds in accordance with the invention, which are selected from the general family, exhibit novel and unexpected properties.

However, in order to obtain these properties the selected compounds must be prepared in accordance with a specific method of manufacture.

The selected compounds comprise a molecule which is formed from a complex of iron $Fe_{II}$ in which said metal $Fe_{II}$ is bonded to a 1-2-4 triazole ligand of the following formula

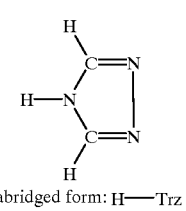

in abridged form: 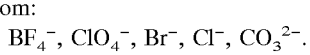

This molecule further comprises an anion which is selected from:

$BF_4^-$, $ClO_4^-$, $Br^-$, $Cl^-$, $CO_3^{2-}$.

Dependent upon the selected anion, these compounds have the following formula:

a) $Fe_{II}(A\text{-}TrZ)_3\,(BF_4^-)_2$
b) $Fe_{II}(H\text{-}Trz)_3\,(ClO_4^-)_2$
c) $Fe_{II}(H\text{-}Trz)_3\,(Br^-)_2$
d) $Fe_{II}(H\text{-}Trz)_3\,(Cl^-)_2$
e) $Fe_{II}(H\text{-}Trz)_3\,(CO_3^{2-})$ In these compounds, a molecule can allow a water molecule $H_2O$ to be present, resulting in the following chemical formulation of the compounds:

a') $Fe_{II}(H\text{-}Trz)_3\,(BF_4^-)_2,\,H_2O$
b') $Fe_{II}(H\text{-}Trz)_3\,(ClO_4^-)_2,\,H_2O$
c') $Fe_{II}(H\text{-}Trz)_3\,(Br^-)_2,\,H_2O$
d') $Fe_{II}(H\text{-}Trz)_3\,(Cl^-)_2,\,H_2O$
e') $Fe_{II}(H\text{-}Trz)_3\,(CO_3^{2-}),\,H_2O$ The presence of said water molecule per molecule of the compound is not indispensable. When said water molecule is present, it is situated in the network, but it is not covalently bonded to the elements of the chemical formulas a'), b'), c'), d'), e'). This water molecule is only bonded by a hydrogen bond to the H-Trz ligand, i.e. the 1-2-4 triazole. When this water molecule is present, it acts on the metal-ligand bonding strength.

To ensure that said water molecule is present in the network, use must be made of a specific method of manufacture.

II METHOD OF MANUFACTURING COMPOUNDS HAVING THE PRECEDING CHEMICAL FORMULATION

For example, to prepare the compound whose chemical formula corresponds to a) $Fe_{II}(H\text{-}Trz)_3\,(BF_4^-)_2$, the following constituents are mixed:

n moles of $Fe(BF_4)_2$, $6H_2O$, which is a salt which is used as a precursor around the central iron $Fe_{II}$ atom, in a solution of pure methanol $CH_3$—Oh, in a concentration of 10 n moles per litre;

and 3n moles of 1-2-4 triazole in a solution of pure methanol $CH_3$—OH, in a concentration of 30 n moles per litre, at ambient temperature, i.e. approximatley 20 to 25° C.

In this method of manufacture, n is a number which is greater than zero.

This mixture is subsequently concentrated under a vacuum, for example at a pressure of approximately 30 mm of mercury, i.e. $4.10^3$ Pa (760 mm.Hg=$10^5$ Pa) while simultaneously bringing this mixture to a temperature in the range between 60 and 80° C., for example, approximately 70° C.

A compound of formula a) $Fe_{II}(H\text{-}Trz)_3\,(BF_4^-)_2$ precipitates very rapidly.

As soon as the precipitate is obtained, it is important to eliminate the methanol solvent as quickly as possible, for example by filtering, to obtain an at least 99 wt. % pure compound.

The compound of the formula $Fe_{II}(H\text{-}Trz)_3\,(BF_4^-)_2$ thus obtained is preserved without washing it or subjecting it to other treatments.

To obtain a water molecule in the network, which leads to a compound of the formula:

a') $Fe(H\text{-}Trz)_3\,(BF_4^-)_2,\,H_2O$ an excess of the precursor of iron, $Fe(BF_4^-)_2$, $6H_2O$, can be used. Instead of n moles of $Fe(BF_4^-)_2$, $6H_2O$, for 3 n moles of 1-2-4 triazole, use can be made, for example, of 2 n or 3 n moles of $Fe(BF_4^-)_2$, $6H_2O$.

To avoid an excess of iron caused by using an excess of the precursor of iron, which can adversely affect the optical and magnetic properties in the case of oxidation, hygroscopic salts, such as $Mg(ClO_4)_2$, K $ClO_4$, $NaClO_4$, can be added in a quantity of 25 to 100 wt. % instead of an excess of the precursor of iron.

In this manufacturing process, those skilled in the art must take care that the methanol solvent is removed completely and rapidly as soon as the precipitate is obtained. In fact, if the molecule $Fe(H-Trz)_3 (BF_4^-)_2$ remains in contact with a small quantity of, for example, several ml of methanol solvent, said molecule is "deprotonated", which results in a compound of the formula:

$$Fe(Trz^-)(H-Trz)(BF_4^-),$$

wherein the metal $Fe_{II}$ is bonded to two ligands, $(Trz^-)$ and (H-Trz), instead of to the single ligand (H-Trz). It is noted that $Trz^-$ is 1-2-4 triazolate.

Thus, the method of preparation which is preferred in accordance with the invention enables the following pure compound to be obtained:

$$Fe(H-Trz)_3(BF_4^-)_2$$

wherein the metal $Fe_{II}$ is bonded to the single 1-2-4 triazole ligand (HTrz). If those skilled in the art do not produce the compound by means of an appropriate method, a mixture of:

$Fe(Trz^-)(H-Trz)_2 (BF_4^-)$ [compound having two ligands $(Trz^-)$ and (H-Trz)]

$+Fe(H-Trz)_3 (BF_4^-)_2$, [compound in accordance with the invention]

is always obtained, in which mixture the main constituent is the compound having two ligands, which comprises triazolate and which has the following formula $$Fe(Trz^-)(H-Trz)_2(BF_4^-).$$

When the above mixture is obtained, the main compound $Fe(Trz^-)(H-Trz)_2 (BF_4^-)$ masks the properties of the compound $Fe(H-Trz)_3 (BF_4^-)_2$ which, consequently, is an "impurity".

However, it is just the compound $Fe(H-Trz)_3 (BF_4^-)_2$ which exhibits the surpising properties in accordance with the invention described herein. Consequently, it is important to obtain this product with the highest possible degree of purity, i.e. the compound exhibits a purity of at least 99 wt. %.

In the above-described manufacturing process, the chemical compound selected in accordance with the invention is obtained in powdered form or in the form of a friable product which can be converted to powder.

An additional technical problem has been encountered, which resides in that the product, if it is white, can turn yellow with time. This can be attributed to the fact that there may be an excess of iron, such as $Fe (BF_4)_2$, in the product. Unbonded iron $Fe^{2+}$ has a tendency to oxidize in the presence of water containing $Fe^{3+}$.

The yellowing of the compound may adversely affect the contrast when the compound is used in the manufacture of display devices and, in addition, oxidation may adversely affect the magnetic properties.

Consequently, the white colour must be stabilized in the finished product. This is achieved by adding to the powder or to the friable product a quantity of less than 5% by weight of a reducing agent, such as ascorbic acid.

When this method is used, all properties of the compound are preserved and the iron excess does not have an adverse effect. Consequently, the product indefinitely retains its perfectly white colour, even in the presence of water, if certain temperature requirements, which will be explained hereinbelow, are met.

III REMARKS a) As stated hereinabove, it is not necessary for the network of the molecule of the compound in accordance with the invention to comprise water. If said network comprises water, a ratio of one water molecule to one molecule of the compound is sufficient.

b) If, in the manufacturing process, instead of the compound comprising $(BF_4^-)$ as the anion, it is desired to provide a compound comprising one of the other anions mentioned hereinabove, such as $ClO_4^-$, $CO_3^{2-}$, $Br^-$, $Cl^-$, the corresponding salt is used as the precursor of the iron nucleus, that is, respectively:

$Fe(ClO_4)_2, 6H_2O$
$Fe(CO_3), 6H_2O$
$Fe(Br)_2, 6H_2O$
$Fe(Cl)_2, 6H_2O$ and the process is continued in the same manner as with $Fe(BF_4)_2, 6H_2O$ salt.

c) In the manufacture of said compounds, other alcohol-like organic solvents can be used instead of methanol.

IV GENERAL PROPERTIES OF SPIN-TRANSITION COMPOUNDS OF THE SUB-FAMILY SELECTED IN ACCORDANCE WITH THE INVENTION

With reference to FIG. 1, the compounds of the above-described sub-family exhibit thermally induced spin transition phenomena.

These spin transitions are accompanied by electronic and structural modifications of the molecules. These modifications cause an abrupt change of the absorption spectrum of the molecules and hence of the colour of the compounds due to the fact that the transitions between the electronic energy levels have become different.

Thus, in the low-spin state (LS) the compounds are dark purple, whereas in the high-spin state (HS) the compounds are chalk-white. In these two states the compounds exhibit a very great colour contrast.

Both the high-spin state and the low-spin state are stable at a temperature close to the so-called critical temperature. The high-spin and low-spin states are stable at this critical temperature in a concomitant manner.

During the spin transitions, these materials exhibit a delay effect caused by the intermolecular cooperativity. This brings about a hysteresis effect.

FIG. 1 shows that said compounds exhibit two potential wells, one of which corresponds to curve A, which is related to the low-spin state, and the other corresponds to the curve B, which is related to the high-spin state. These potential wells A and B are separated by a potential barrier. The bottom Ao of the potential well A(LS) corresponds to a first energy level $H_{LS}$ and to a first metal-ligand distance $D_{LS}$, and the bottom Bo of the potential well B(HS) corresponds to a second energy level $H_{HS}$ and to a second metal-ligand distance $D_{HS}$.

The difference in energy between the bottom levels Ao and Bo of said two potential wells is referred to as $\Delta H = H_{HS} - H_{LS}$.

An increase of the temperature of one of the selected compounds which, at the outset, is in the low-spin state (LS) in which the electrons are trapped in the first potential well A induces excited high-spin states. However, these excited states are not stable and the electrons relax back, via allowed transitions, while following a main relaxation path which is that of the second potential well B, which corresponds to a perfectly stable high-spin state.

Consequently, the electrons remain trapped in the second potential well B and do not spontaneously return to the first potential well A, which corresponds to the low-spin state. To return to the low-spin state, the compounds must be cooled.

Figure 2:
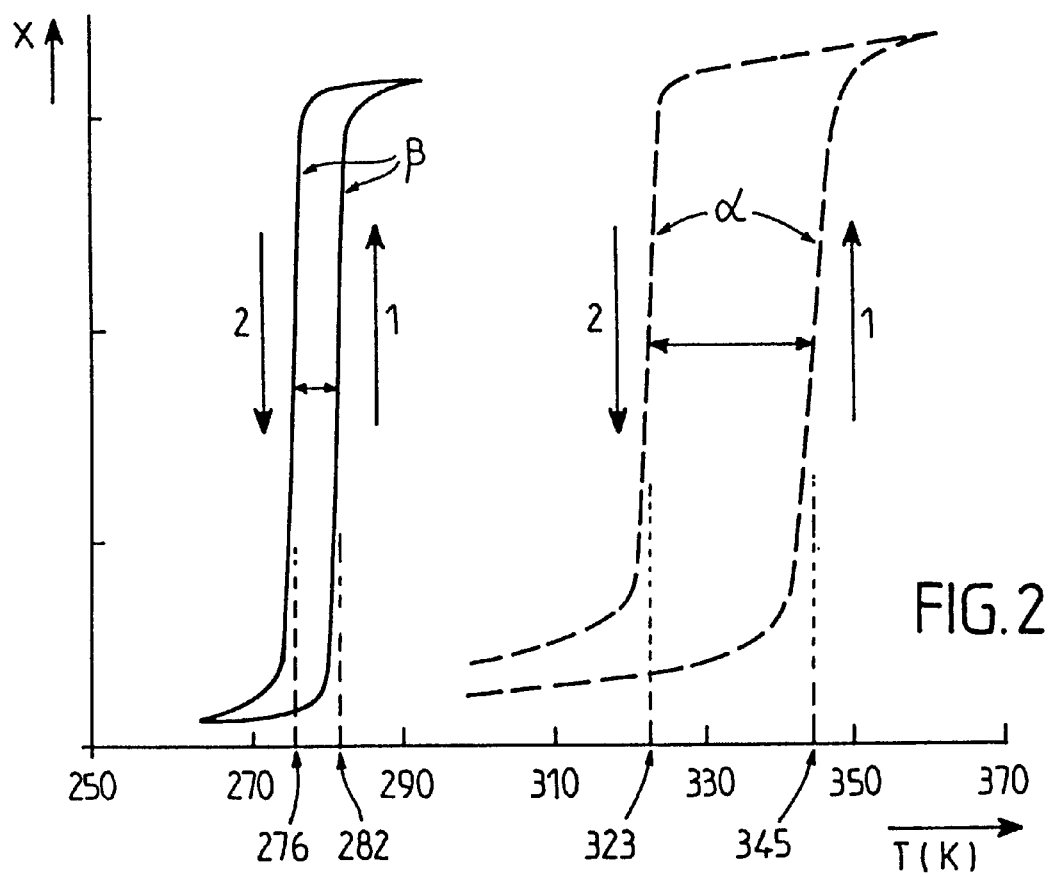
FIG. 2 shows the hysteresis cycles, corresponding to each of the states α and β, of compounds in accordance with the invention, wherein X, being the molar fraction of the material which has undergone a transition at the temperature T, is plotted on the Y-axis and T, being the temperature in degrees Kelvin, is plotted on the X-axis.

In FIG. 2, the curve a represents a hysteresis cycle of the compound of the formula a) $Fe(H-Trz)_3 (BF_4^-)_2$ which is directly obtained by the above-described method. Hereinbelow it will be used as an exemplary compound.

The molar fraction X of the material which has undergone a transition at a temperature T (in degrees Kelvin) is plotted on the Y-axis and the temperature T is plotted on the X-axis. The curve α of FIG. 2 shows that this compound has a hysteresis cycle in the range between:

$T_{\alpha 1}$=345 K for the high-spin transition temperature, and $T_{\alpha 2}$=323 K for the low-spin transition temperature. At temperatures below the temperature $T_{\alpha 2}$, the compound is in the low-spin state (LS), and at temperatures above the temperature $T_{\alpha 1}$, the compound is in the high-spin state (HS).

At a temperature $T_{\alpha c}$≈334 K, being the mean critical temperature, the high-spin and low-spin states previously induced by a suitable thermal variation remain stable for an indefinite period of time.

By virtue of the teachings of Patent Application EP 0 543 465, these properties were foreseen.

However, the selected compound a) exhibits remarkable effects under the conditions which will be described hereinbelow.

A first surprising effect is that if the compound of the formula a) is brought to a temperature T which is higher than or equal to a temperature which is referred to as the first reference temperature To=440 K said compound undergoes a change in crystalline phase. The new crystalline phase obtained by heating to a temperature which is higher than or equal to To=440 K will hereinafter be referred to as crystalline phase β. The crystalline phase of the compound which is directly obtained by the above method and of which the properties have been described hereinabove is referred to as crystalline phase α.

A second, surprising effect is that the compound a) in its new crystalline phase β also exhibits a spin transition with delay effect, but at different temperatures than in the crystalline phase α. This spin transition leads to the hysteresis cycle represented by curve β in FIG. 2. In the crystalline phase β, this compound exhibits a hysteresis cycle which ranges between:

$T_{\beta 1}$=282 K for the high-spin transition temperature, and $T_{\beta 2}$=276 K for the low-spin transition temperature.

In the low-spin state, the compound is purple in phase β as well as in phase α, whereas in the high-spin state, the compound is pure white.

Consequently, if use is made of a compound at an ambient temperature $T_R$=290 K, referred to as second reference temperature, the compound is in the low-spin state of phase a and of a purple colour, since $T_R < T_{\alpha 2}$.

If the compound is heated to a temperature T, such that $T_{\alpha 1} < T < To$, i.e. 345 K<T<440 K, the compound turns white because it is in the high-spin state of phase α.

If the temperature is then lowered to the ambient temperature $T_R$=290° K, the compound turns purple again because it returns to the low-spin state of phase α.

If the compound is then heated to a temperature in excess of the first reference temperature To, i.e. higher than or equal to 440 K, the compound turns white because it is in the high-spin state of phase β.

However, once the compound has been heated to a temperature above To, and its temperature is then reduced to the ambient temperature $T_R$=290 K, the compound remains white: it remains in the high-spin state of phase β because $T_R > T_{\beta 1}$.

The compound can be made purple again by cooling it to the low-spin transition temperature $T_{\beta 2}$ of phase β, i.e. it must be cooled to 276 K or lower.

All of the selected compounds of the formulas a) to e) and a') to e') have the same properties and the same surprising effects as the above-described compound a).

V DEVICE FOR WRITING, STORING AND DISPLAYING DATA

A device for writing, storing and displaying data, which comprises at least one of the selected compounds in accordance with the invention is described by way of example. This device comprises:

A) An Active Medium and a Support

To provide a device for writing, storing and displaying of data, it is first of all necessary to prepare an active medium which comprises one or more spin-transition chemical compounds, as described hereinabove, and which medium is bonded to a support.

In a first example, the active medium can favourably be formed from a thin film of the chemical compound which is directly deposited on the support. For this purpose, the film can be manufactured by evaporating a solvent which comprises the powder of the chemical compound selected.

In a second example, the chemical compound in powdered form can be embedded in a transparent material. This material may be a transparent, polymerizable resin which is deposited on the support.

The support may be a plate of any contour form or dimensions, such as square, rectangular, polygonal, circular, oval, etc. In particular, plates of very large dimensions and very small dimensions can be used. The support may be rigid or flexible. In addition, a large number of non-brittle, low-cost materials, for example a synthetic material, can very suitably be used as the support for the spin-transition compounds.

The device may be operated in the reflection mode or in the transmission mode. If the device is operated in the transmission mode, the support may consist of a transparent synthetic material.

In the device for writing, storing and displaying, the active medium comprises display regions and background regions.

B) A Thermal Addressing System

The device must comprise, inter alia, means for locally changing the temperature of the active medium or for changing the temperature of the entire active medium.

Said means consist of a thermal addressing system which serves to change the temperature of the display regions and background regions.

B1) This thermal addressing system comprises, on the one hand, heating means, such as:

a heating pencil, for example a laser beam in the infrared range of the spectrum or a laser having a wavelength of 520 mm or a pencil of the resistive-heating type, a matrix of resistive-heating contacts which are addressed in accordance with x, y-patterned lines and columns.

Said matrix of resistive-heating contacts may comprise two intersecting networks of electrodes. In a particular embodiment, the active medium may be disposed between said two electrode networks, with a heat-dissipating system being provided. In a favourable embodiment, the electrodes may be transparent and made, for example, of InSnO (indium-tin oxide). In this particular embodiment, the system for writing, storing and displaying can operate equally well in the transmission mode as in the reflection mode.

If the intended use does not require the electrodes to be transparent, they can be made of all metals which are customarily used for this purpose.

The advantage of the system which includes a matrix of x,y electrodes is that it can receive and display messages, data or informations which are coded in x, y.

In accordance with the invention, the system made in this manner can for example be used to realise an emission-reception device which is capable of displaying the transmitted message.

B2) This thermal addressing system comprises, on the other hand, cooling means, such as:
   means for cooling the support as a whole,
   means for locally cooling the support, such as Peltier elements which are used to selectively cool the display regions or the background regions.

VI METHOD OF EMPLOYING THESE DEVICES

FIG. 3 represents a device for writing, erasing and displaying information, which is produced by means of the compound a) described hereinabove to form an active medium.

This device enables a screen consisting of a support covered with the active medium containing the compound a) to be locally heated or cooled to various temperatures $T_{\alpha 1}$, $T_{\alpha 2}$, $T_R$, $T_{\beta 1}$, $T_{\beta 2}$, To, in at least one display region and one background region. In the example illustrated in FIG. 3, the screen comprises a single display region which corresponds to a geometric pattern, in this case a letter of the alphabet "Z".

Said heating and cooling means enable the following thermal perturbations to be successively, locally applied to the active medium of this screen, in the displays region, at the location of the pattern:

A) The starting temperature is the ambient temperature $T_R$=290 K; the screen is uniformly purple (FIG. 3A); the entire screen, i.e. the display region and the background region, is in the low-spin state of phase α.

B) The display area of the pattern is brought to a temperature T,
   $T_{\alpha 1}$<T<To,
i.e. 345 K<T<440 K: the pattern is white on a purple background (FIG. 3B); the area of the pattern is in the high-spin state of phase α; the background remains in the low-spin state of phase α.

C) The temperature of the area of the pattern is lowered to the ambient temperature $T_R$=290 K, the screen becomes uniformly purple again (FIG. 3C); the entire screen is in the low-spin state of phase α.

Figure 3A:
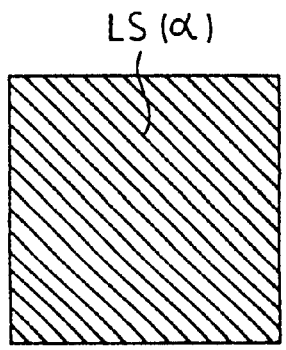
FIG. 3 show the different stages of writing, storing or erasing by means of the compounds in accordance with the invention.
Figure 3B:
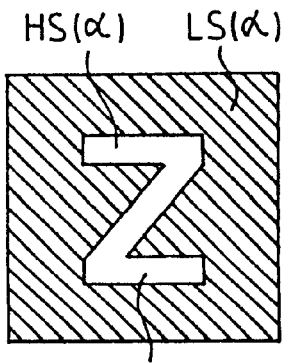
Figure 3C:
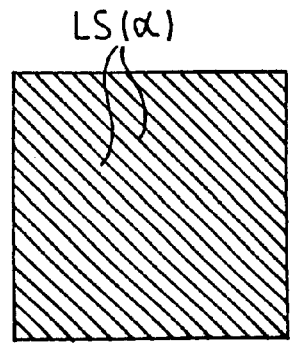
Figure 3D:
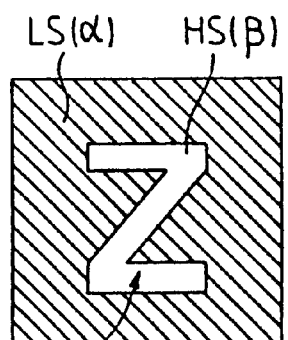

D) The area of the pattern is brought to the high temperature T which is higher than or equal to To=440 K; the area of the pattern turns white because it is in the high-spin state of phase β; the rest of the screen is purple because it remains in the low-spin state of phase α (FIG. 3D).

Figure 3E:
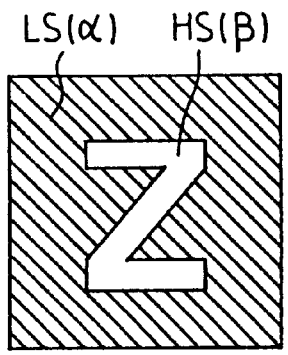

E) The area of the pattern is cooled to the ambient temperature $T_R$=290 K; the area of the pattern remains white because it is still in the high-spin state of phase β; the background of the screen remains purple (FIG. 3E).

Figure 3F:
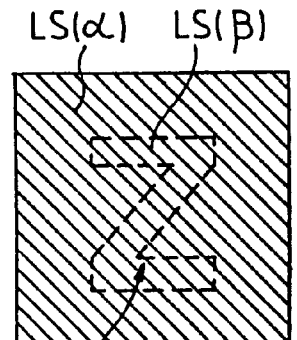

F) The temperature of the area of the pattern is reduced to a temperature which is lower than or equal to $T_{\beta 2}$=276 K; the area of the pattern turns purple again (FIG. 3F).

The third surprising effect resides in that, despite the fact that the screen has become entirely purple again the pattern is not erased: the information related to this pattern is only hidden. The background of the screen has remained in the low-spin state of phase a, while the area of the pattern is in the low-spin state of phase β.

G) The area of the pattern is reheated to the ambient temperature $T_R$=290 K, and as a result thereof the area of the pattern reappears as a white-coloured part on a purple background because this area is now in the high-spin state of phase β.

Figure 3G:
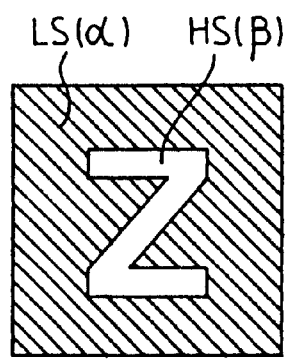
Figure 3H:
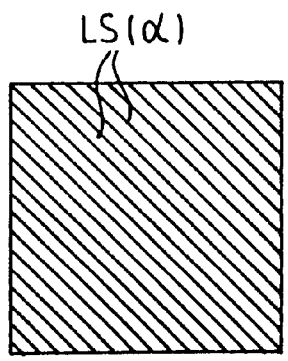

By virtue of these surprising novel properties of the compounds selected in accordance with the invention, the information has been stored in steps D and E, hidden in step F and displayed again in step G (FIG. 3G).

H) the information which has reappeared in step G), in which step the area of the pattern is in the high-spin state of phase β, is spontaneously erased after some time as a result of the fact that the compound returns to phase α. This period of time varies and depends on which product from the list of selected products is used.

This period of time may be several hours or even several days. Thus, erasure takes place as a result of a spontaneous return from phase β to phase α.

The erasing operation can alternatively be induced at will by means other than thermal means.

Thus, the compound is free of information again and can be used for a new writing step.

As already known, steps A, B and C enable the compound in phase a to be used for displaying information by determining the instant when the information is written and the instant when the information is totally erased. The information can be stored in or originate from a supplementary device other than the active medium of the screen. Consequently, the active medium produced by means of the compound in phase α only has a display function.

Steps D to G enable the compound in phase β to display information, store said information in the active medium of the screen and, subsequently, hide said information and re-display it on the screen at any time. Consequently, in addition to the display function, the active medium of the screen also has a storage function.

The above-described properties of the compound of the chemical formula a) also apply to the other compounds b), c), d), e) and a') to e').

VII APPLICATIONS AND ADVANTAGES OF THE DEVICES FOR WRITING, STORING AND DISPLAYING

A display device which has been produced by means of an active medium in accordance with the invention can advantageously be used to manufacture a display screen for a smart card at very low cost. As described hereinabove, the active medium may be bonded to a synthetic support, thereby forming a system which is particularly well suited to cooperate with another synthetic support, such as the support of the smart card. In addition, the active medium bonded to its own support can be extremely thin. Consequently, the use of this active medium/support system for the manufacture of a screen which can display the data stored in a smart card is very favourable.

Such a display system can also be used in many other devices in which the fragility of a screen of liquid crystals is unfavourable, particularly for displaying data concerning the functioning of electrodomestic appliances. The display device can also be used for calculators, audio and video equipment, games etc., and in particular for monitor screens, screens for the purposes of public address, urban signposting, airport information posting etc. Such a display device could be used instead of a liquid crystal display device in a large number of applications, but it is not limited thereto, as it can be manufactured on very large supports.

An application of the display system could be, for example, of the "magic tablet" type. This tablet is a device which employs a heating pencil in combination with an active medium comprising the selected compounds. Such a magic tablet could be used to visualize the data entered into an information storage device by means of a classic tactile tablet.

What is claimed is:

1. A spin-transition parent compound in powder form, comprising a network having a molecule which is formed from a complex in which iron ($Fe_{II}$) is bonded to a 1-2-4 triazole ligand (H-Trz), said molecule further comprising an anion $(A)_2$ which is selected from $BF_4^-$, $ClO_4^-$, $Cl^-$, $Br^-$, $CO_3^{2-}$, and, dependent upon the anion, said molecule corresponding to the formula:

a') $Fe_{II}(H-Trz)_3 (BF_4^-)_2, H_2O$
b') $Fe_{II}(H-Trz)_3 (ClO_4^-)_2, H_2O$
c') $Fe_{II}(H-Trz)_3 (Br^-)_2, H_2O$
d') $Fe_{II}(H-Trz)_3 (Cl^-)_2, H_2O$
e') $Fe_{II}(H-Trz)_3 (CO_3^{2-}), H_2O$ wherein one water molecule per molecule of the iron complex is present in the network, said water molecule only being bonded to the 1-2-4 triazole ligand (H-Trz) by a hydrogen bond, and wherein said compound also comprises a hydroscopic salt in a quantity of from 25 to 100% of the weight of the compound, to ensure that said water molecule is present in the network.

2. A compound as claimed in claim 1, in which the hygroscopic salt is iron borofluoride, magnesium perchlorate, potassium perchlorate, sodium perchlorate, or a mixture of said salts.

3. A compound as claimed in claim 2 comprising a reducing agent in a quantity below 5 wt. % of said compound.

4. A compound as claimed in claim 1, comprising a reducing agent in a quantity below 5 wt. % of said compound.

5. A compound as claimed in claim 4 wherein the reducing agent is ascorbic acid.

6. A spin-transition parent compound in powder form, comprising a network having a molecule which is formed from a complex in which iron ($Fe_{II}$) is bonded to a 1-2-4 triazole ligand (H-Trz), said molecule further comprising an anion $(A)_2$ which is selected from $BF_4^-$, $ClO_4^-$, $Cl^-$, $Br^-$, $CO_3^{2-}$, and, dependent upon the anion, said molecule corresponding to the formula:

a) $Fe_{II}(H-Trz)_3 (BF_4^-)_2$
b) $Fe_{II}(H-Trz)_3 (ClO_4^-)_2$
c) $Fe_{II}(H-Trz)_3 (Br^-)_2$
d) $Fe_{II}(H-Trz)_3 (Cl^-)_2$
e) $Fe_{II}(H-Trz)_3 (CO_3^{2-})$ and wherein said compound further comprises a reducing agent in a quantity below 5 wt. % of said compound.

7. A compound as claimed in claim 6, in which the reducing agent is ascorbic acid.

8. A spin-transition parent compound in powder form, comprising a network having a molecule which is formed from a complex in which iron ($Fe_{II}$) is bonded to a 1-2-4 triazole ligand (H-Trz), said molecule further comprising an anion $(A)_2$ which is selected from $BF_4^-$, $ClO_4^-$, $Cl^-$, $Br^-$, $CO_3^{2-}$, and, dependent upon the anion, said molecule corresponding to the formula:

a') $Fe_{II}(H-Trz)_3 (BF_4^-)_2, H_2O$
b') $Fe_{II}(H-Trz)_3 (ClO_4^-)_2, H_2O$
c') $Fe_{II}(H-Trz)_3 (Br^-)_2, H_2O$
d') $Fe_{II}(H-Trz)_3 (Cl^-)_2, H_2O$
e') $Fe_{II}(H-Trz)_3 (CO_3^{2-}), H_2O$ wherein one water molecule per molecule of the iron complex is present in the network, said water molecule only being bonded to the 1-2-4 triazole ligand (H-Trz) by a hydrogen bond, and wherein said compound further comprises a reducing agent in a quantity below 5 wt. % of said compound.

* * * * *